United States Patent
Manly et al.

[11] Patent Number: 5,931,795
[45] Date of Patent: Aug. 3, 1999

[54] METHOD FOR EVALUATING HUMAN BONE STRENGTH

[76] Inventors: Philip Manly, 5556 Opihi St., Honolulu, Hi. 96821; Jerry M. Hoorneman, Van Dederzaan 19 38FiTD, Hoevelaken, Netherlands

[21] Appl. No.: 08/966,103

[22] Filed: Nov. 7, 1997

[51] Int. Cl.[6] .................................................. A61B 5/103
[52] U.S. Cl. ........................................................ 600/587
[58] Field of Search .................................. 600/587, 595; 33/512; 73/572, 596; 378/53, 54, 88, 89

[56] References Cited

U.S. PATENT DOCUMENTS

| | | | |
|---|---|---|---|
| 4,421,119 | 12/1983 | Pratt, Jr. .................................... | 600/587 |
| 4,754,763 | 7/1988 | Doemland ................................ | 600/587 |
| 4,976,267 | 12/1990 | Jeffcott et al. ........................... | 600/587 |
| 5,006,957 | 4/1991 | Steele ....................................... | 600/587 |
| 5,138,553 | 8/1992 | Lanza et al. ............................. | 600/587 |
| 5,348,009 | 9/1994 | Ohtomo et al. .......................... | 600/407 |
| 5,749,363 | 5/1998 | Ishii et al. ................................ | 600/587 |
| 5,800,363 | 9/1998 | Cheng et al. ............................ | 600/587 |

*Primary Examiner*—Max Hindenburg
*Assistant Examiner*—Charles Marmor, II
*Attorney, Agent, or Firm*—Richard D. Multer

[57] ABSTRACT

A method for assessing an individual's risk of bone fracture by evaluating the bone strength of the individual. The steps include: (1) measuring the bone mineral content of an individual's radius or other bone with a cortical wall (such as the femoral neck or the phalanges) by dual energy densitometry, (2) calculating the effective average cortical wall thickness (CWT) and bending breaking resistance indicator (BBRI) of the bone from the bone mineral content and bone width, and (3) using a combination of the CWT and BBRI to estimate the bone strength of the individual. The bone mineral content can also be determined by microdensitometry measurements of an x-ray of the bone of interest. The fracture risk can be presented by assigning color values to different ranges of CWT and BBRI and by using a combination of these color values to indicate bone strength. The values of CWT and BBRI can also be plotted against young normal age-matched normal values as further visual indications of fracture risk.

10 Claims, 3 Drawing Sheets

METHOD FOR EVALUATING HUMAN BONE STRENGTH

TECHNICAL FIELD OF THE INVENTION

The present invention related to novel, improved methods for evaluating the strength of human bones.

BACKGROUND OF THE INVENTION

Due to the rapid increase in the number of elderly people in the population, bone disorders such as osteoporosis and osteomalacia are becoming more common. Osteoporosis generally refers to a disorder wherein the amount of bone mineral in the skeleton decreases, and the weakened bone is more susceptible to fracture. Osteomalacia is a softening of the bones generally caused by a deficiency of vitamin D. Fractures of the spine (crush fractures) and of the radius (Colles fractures) or femoral neck can decrease the quality of life or shorten the life of the increasing numbers of elderly in the population. However, there are steps which can be taken to reduce the probability of such injuries if the individual is known to be at risk. Consequently, an accurate, cost-effective method for evaluating an individual's susceptibility to bone fracture is needed.

In present methods of assessment, bone mineral content or bone mineral density are used to estimate the fracture risk from osteoporosis. Such methods have the disadvantage that they do not completely describe the mechanical strength changes that occur in the skeleton with age and therefore only approximately estimate the increased risk of fracture in an aging individual.

The typical method for determining bone mineral content employs photon absorptiometry. In this method, a beam of x-rays is passed through the bone being measured, either in a rectilinear fashion using a pencil beam of x-rays, or in a scan with a fan-like beam of x-rays. The attenuation of the x-ray beam is used to calculate the amount of bone mineral present through the use of the attenuation formula for x-rays:

$$I = I_o x e^{-\mu_x x} \qquad (1)$$

where I=attenuated x-ray beam
  $I_o$=unattenuated x-ray beam
  $\mu$=lineal attenuation coefficient of absorber
  x=thickness of absorber Bone strength, however, does not depend only on bone mineral content. Bone mineral content is certainly a major factor in determining bone strength, but strength is also affected by the mechanical structure of the bone. In a simple sense, if the long bones of the body were thought of as pieces of tubing, the bone mineral content would relate to the total amount of material in the tubing per unit length. However, the mechanical strength of such a tubing would also be significantly affected by the tubing diameter and tubing thickness. These diameter and thickness factors are not accounted for in a simple measurement of bone mineral content.

Thus, there is an existent and continuing need for a better method of assessing bone strength, especially a method which takes into account not only the total amount of material present (bone mineral content), but also the geometrical distribution of the material present.

SUMMARY OF THE INVENTION

Disclosed herein is a novel and improved method for assessing fracture risk which overcomes the above-discussed limitations of existing protocols which employ bone mineral content measurement. This improved method provides an assessment of fracture risk that is more sensitive and more specific than existing methods.

Specifically, the present invention relates to an improved method for estimating fracture risk based on an assessment of bone mineral density and bone width. More specifically, the present invention is a method for estimating bone strength in which the effective Cortical Wall Thickness (CWT) of an individual's bone is determined from measurements of the bone mineral density of a long bone anywhere in the body either by photon densitometry or by microdensitometry of an x-ray and may be applied to all long bones. Then, an estimate of the bending resistance of the bone is obtained through calculation of the Bending Breaking Resistance Indicator (BBRI). BBRI is the variable portion of the mechanical engineering formula for breaking bending resistance, and it contains the second moment of inertia.

The objects, features, and advantages of the invention will be apparent to the reader from the foregoing and the appended claims and as the ensuing detailed description and discussion proceeds in conjunction with the accompanying drawing.

DETAILED DESCRIPTION OF THE INVENTION

In the present invention bone strength is estimated from an in vivo bone density measurement and an in vivo measurement of bone width, employing the following steps:

(1) Measuring mineral density (in units of mg/cm$^2$) with a x-ray or photon densitometer or by microdensitometry of a calibrated x-ray image of the bone;

(2) Determining the diameter of the bone;

(3) Calculating the effective Cortical Wall Thickness (CWT) from the bone mineral density measurement and the bone diameter and from the average density of compact bone in humans; Such assessment employs the Specific Density (SD) of laminar cortical bone. Such SD is a constant for adult human bone. Observed variations in the apparent Specific Density are due to Haversarian channels and cortical porosity.

(4) Calculating the Wall/Lumen Ratio and Cortical Index from the CWT and bone diameter;

(5) Calculating the Bending Breaking Resistance Indicator (BBRI) as the variable portion of the mechanical engineering expression for breaking bending resistance. This expression contains the second moment of inertia for the bone; and (6) Calculating an estimate of bone strength from a combination of the above factors of CWT, Wall/Lumen Ratio, Cortical Index, and BBRI. The results may be presented in numerical form, by graphical comparison with age-matched normal values, or by use of a color-coded system that references each parameter to age-matched normal values.

Figure 1:
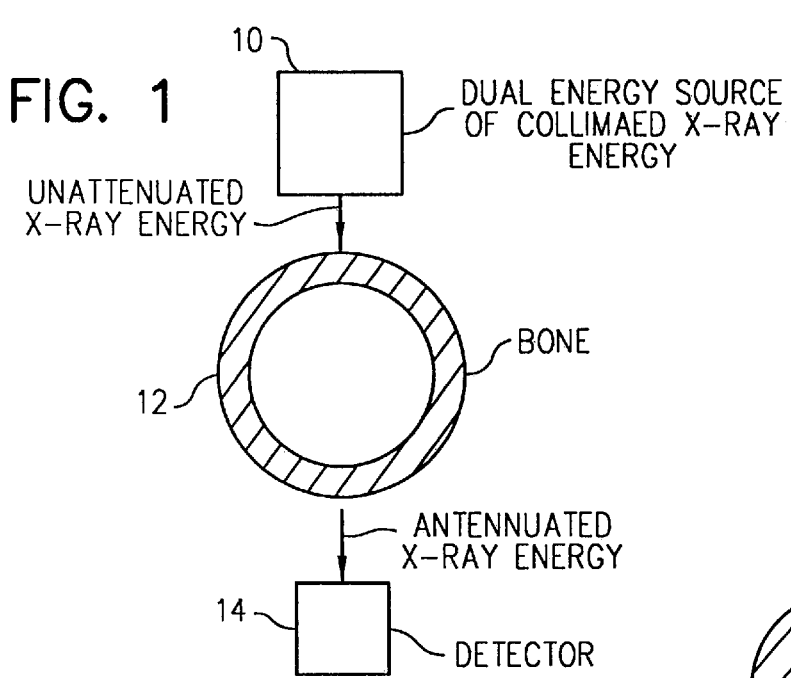
FIG. 1 is a pictorial representation of the x-ray apparatus employed to assess bone strength in accord with the principles of the present invention.

Referring now to FIG. 1, a preferred method of determining bone density employs rectilinear dual energy x-ray absorptiometry. An apparatus consisting of a source 10 of x-rays is positioned on the opposite side of the bone 12 from a detector 14 capable of measuring the x-ray photons that pass through the bone being measured. A collimator on the x-ray source restricts the beam of x-rays to a very narrow "pencil beam" of x-rays that traverse the bone being measured and are detected by the detector. With the pencil beam of x-rays being very small, the physical size of the bone can be accurately measured.

The x-ray source 10 and detector 14 are held in position opposite each other as shown in FIG. 1 and moved at uniform speed across the bone being measured at right angles to the major axis of the bone. As the beam traverses denser portions of the bone, more of the x-rays are attenuated by the bone according to the exponential formula for x-ray attenuation.

$$I = I_o x e^{-\mu x} \quad (2)$$

Where: I=attenuated flux
$I_o$=unattenuated flux
$\mu$=mass attenuation coefficient for the material being scanned
x=mass of attenuating material present A complete traverse of the bone being evaluated by source 10 and detector 14 is called one row of measurement. For each row of measurement the count rate from the detector as a function of position of the source 10/detector 14 across bone 12 is converted to a representation of the bone density.

Alternately, the attenuation measurements can be made with an x-ray beam collimated to a core and an area detector. In this case, the x-ray beam and detector do not traverse over the bone being measured, rather different sections of the detector receive attenuated x-rays simultaneously through different parts of the bone. Thus, the end result is the same—a representation of bone density as a function of position over a two dimensional area—but without movement of the x-ray source and detector.

Figure 2:
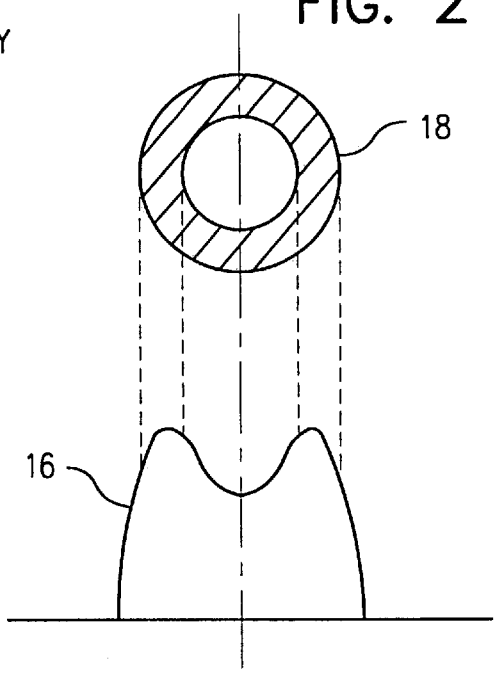
FIG. 2 is a cross-sectional density profile from a single rectilinear scan on a distal radius using dual energy x-ray densitometry to obtain measurements representative of bone density, a parameter employed in assessing bone strength in the method of FIG. 1.

Curve 16 in FIG. 2 is a representative plot of bone density as a function of position across the illustrated bone 18 of FIG. 2 for a cortical bone such as the proximal radius. The total bone content measured in grams is also reported.

Curve 16 represents the density of the bone. However, since the rectilinear scanner cannot measure the actual thickness of the bone, the results of the measurement are reported as a number proportional to the area density, measured in units of mg/cm² or g/cm². This number is not the actual volumetric density, which would be indicated in units of mg/cm³ or g/cm³.

The tissue surrounding the bone also attenuates the x-rays to an extent that can affect the results of the bone density indication. When dual energy absorptiometry is used to make the bone measurement, the effect of the tissue is accounted for or nullified by scanning the bone simultaneously at two different x-ray energies.

The attenuation coefficients for bone and tissue are different for different x-ray energies. By measuring the attenuation through the bone and tissue simultaneously at two different photon energies, the contribution of the tissue to the attenuation of the photon beam can be corrected for. Thus, curve 16 in FIG. 2 gives a true indication of the area density of the bone being measured.

Figure 3:
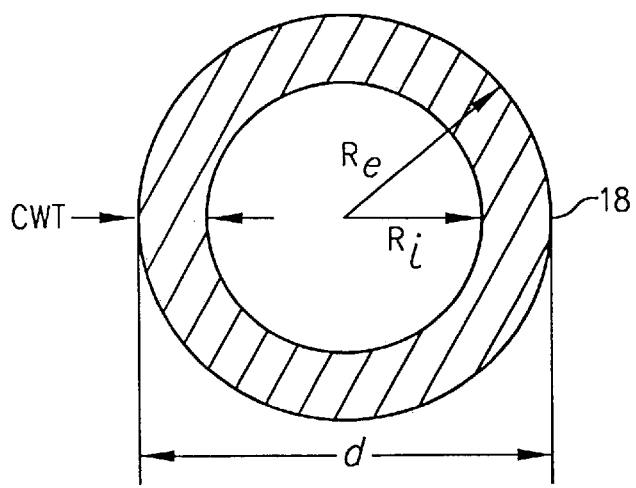
FIG. 3 illustrates a cross-section of the proximal radius, showing the terms for bone diameter, cortical wall thickness, effective average inner radius, and effective average outer radius.

The area density profile as shown in FIG. 2 is translated into a three dimensional description of the bone (see FIG. 3 in which the bone being evaluated is again identified by reference character 18) in terms of average diameter, cortical wall thickness, and volumetric density so that the second moment of inertia can be calculated.

Specifically (step 2), the effective bone radius is calculated from the formula:

$$R_e = D/2.33 \, SF \quad (3)$$

Where $R_e$=effective average bone radius
D=measured bone diameter
SF=shape factor For a perfectly round bone, the shape factor is unity. For other bone shapes, which are different for bones in different parts of the body, the shape factor is empirically determined.

The measured bone diameter is calculated from the bone density profile curve 16 by either finding the point at each end of the curve where the curve rises significantly above the background or by fitting a straight line to the beginning and ending parts of the curve and determining the location at which they intersect with the horizontal axis.

The volumetric density of the compact bone has been determined from experimental measurements to be a constant value (see Osteoporosis Int (1991) 1:76–80). This makes it possible to translate the two dimensional, measured bone density profile into a three dimensional estimation of parameters used to calculate the second moment of inertia of the bone.

Next, the inner radius of the compact bone is calculated according to a formula derived in the following manner:

$$\text{Bone volume} = \frac{BMC}{SD} = \Pi \times (R_e^2 - R_i^2) \times L \quad (4)$$

where BMC =measured bone mineral content in grams
SD=specific density of compact bone (a value that is constant for a particular long bone and is constant for a particular individual)
$R_e$=effective bone outer radius (calculated in accord with (2) above)
$R_i$=effective bone inner radius
L=bone length of measured segment
$\Pi$=pi (3.14159 . . . )

Solving for the unknown radius $R_i$, formula (4) becomes $$R_i = \sqrt{R_e^2 - \frac{BMC}{\Pi \times SD \times L}} \quad (5)$$

with the terms as defined above.

With both the effective outer radius and effective inner radius now calculated, the wall lumen ratio and cortical wall thickness (steps 3 and 4) can be calculated as follows:
Thus:

$$CWT = R_e - R_i \quad (6)$$

where CWT=cortical wall thickness (formula (4))

Re = effective average outer radius
R_i = effective average inner radius (formula (5))

$$WLR = \frac{CWT}{R_i}$$

where: WLR = wall lumen ratio
CWT = cortical wall thickness (calculated above)
R_i = effective average inner radius (calculated above)

The next step (No. 5) is to calculate the bending breaking resistance indicator (BBRI). The BBRI is proportional to the bending moment of resistance W for a hollow circular cross section and is defined by the formula $$BBRI = \frac{(R_e^4 - R_i^4)}{R_e} \quad (8)$$

where: $R_e$ = effective average outer radius of the bone being evaluated
$R_i$ = effective average inner radius of the bone being evaluated Finally, the volumetric ($BMD_v$) and cortical index (CI) can be calculated:

$$BMD_v = \frac{BMC}{R_e^2}$$

BMC = bone mineral content in grams/cm
Re = effective average bone outer radius $$CI = \frac{CWT}{R_e}$$

Figure 4:
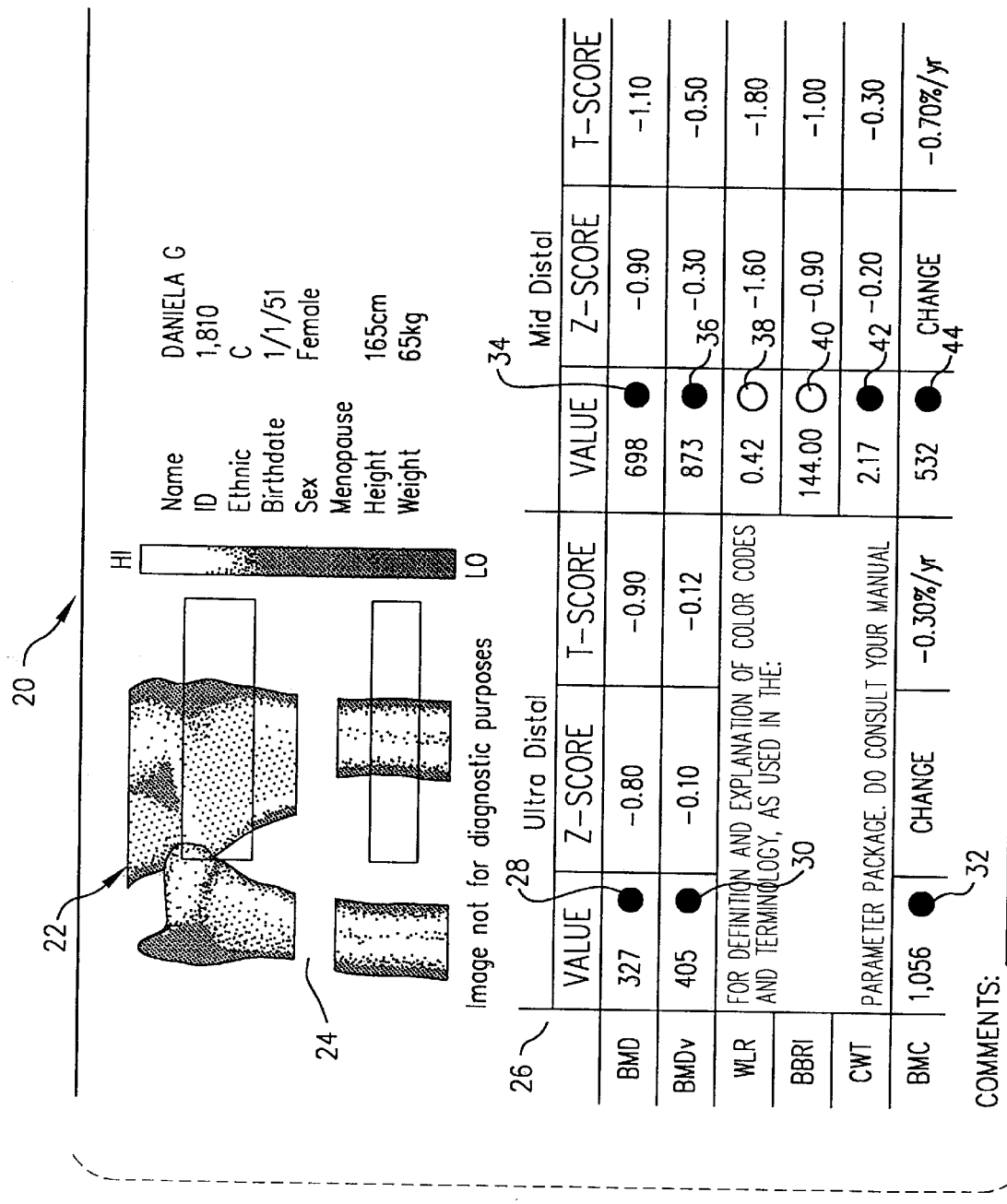
FIG. 4 illustrates a sample report for a bone densitometry study conducted in accord with the principles of the present invention; this report shows how the various parameters of interest are reported.

These parameters, along with bone mineral content and bone mineral density, are presented to the user in the form of a report such as the one identified in FIG. 4 by reference character 20. Report 20 also displays the density image 22 of the bone being calculated with the area of analysis 24 superimposed over the density image. The report also lists information for the patient such as name, identification number, ethnic background, birth date, sex, height, weight, and, if the patient is a female, whether she has undergone menopause.

In the numerical section 26 of the report, the traditional parameters of bone mineral density (BMD) volumetric bone density BMD (v), and bone mineral content (BMC) are presented. The BMD is compared against the BMD for young normal (given in the T-score) and against an aged matched normal (given in the Z-score). The T-score can be used in diagnosing osteopenia or osteoporosis according to the World Health Organization (WHO) definition. The Z-score indicates how the individual fares compared with her aged-matched cohort. The BMC value is compared with previous measurements of BMC as an indication of increase or decrease in bone mineral since BMC of the proximal radius correlates well with total body calcium.

Bone mineral content (BMC) is the weight of a one centimeter slice along the length of the bone undergoing evaluation. BMC is given in the units mg/cm.

Figure 5:
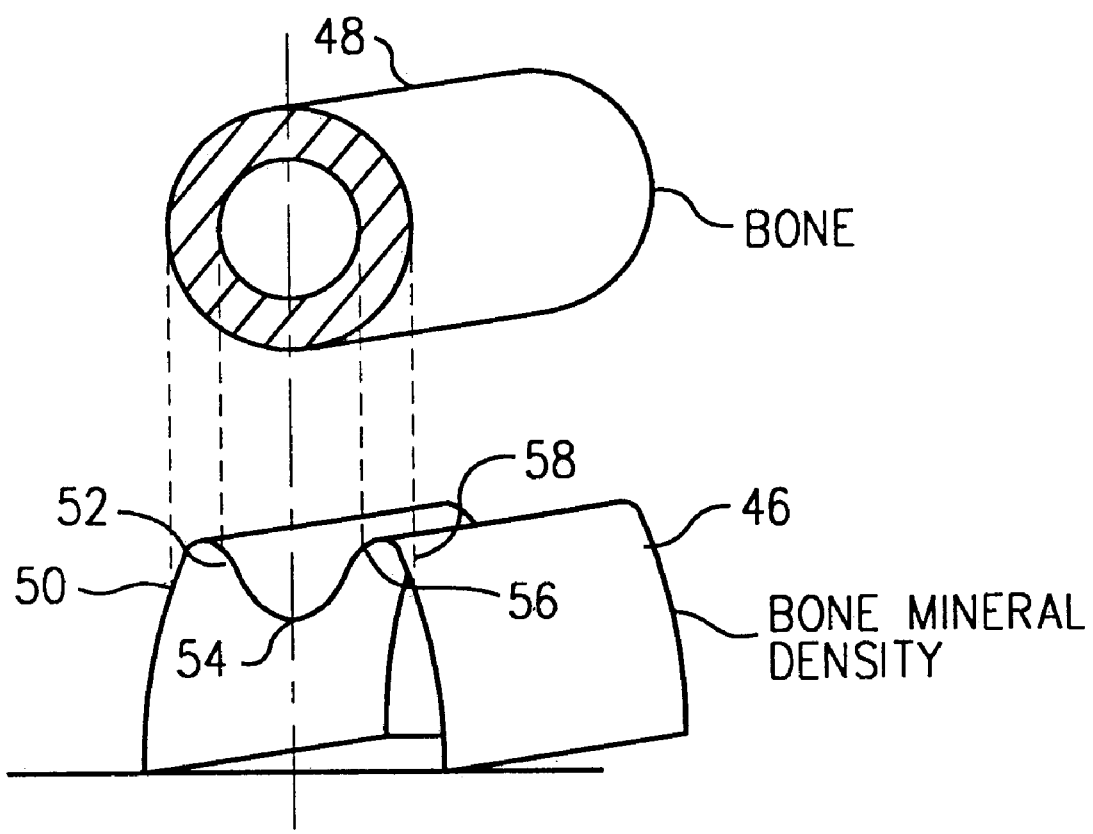
FIG. 5 depicts pictorially the variation of bone mineral density across the section of a bone.

Bone mineral density (BMD) is the weight of the bone divided by the product of: the length of the section and the diameter. Since rectilinear scanners can only measure the length and width of the bone, they can only give the unit density in terms of grams/cm $^2$(or mg/cm$^2$) at a particular location along the bone. Points 50 . . . 58 across the curve 46 under the bone section 48 in FIG. 5 represent the measured BMD at these representative particular points along the bone.

If it were possible to measure the actual density of bone in a small volume, the result would be the volumetric density, or BMD(v). The units of BMD(v) are grams/cm$^3$ or mg/cm$^{3.}$ In addition to the traditional parameters of BMD and BMC, the parameters of Wall/Lumen Ratio (WLR), Cortical Wall Thickness (CWT), and Bending Breaking Resistance Indicator (BBRI), are given along with their respective Z-score and T-scores. These factors can be used as additional indicators of the strength of the bone and its susceptibility to future fracture.

Small color dots such as those identified by reference characters 28 . . . 44 may be displayed next to the values for BMD, WLR, BBRI, CWT, and BMC. These dots are colored green, yellow, or red to identify low, moderate, and high risks of fracture.

We claim:

1. A method for evaluating human bone strength comprising the steps of:
    measuring the mineral density and mineral content of a bone having a cortical wall;
    measuring the width of said bone;
    determining the effective average cortical wall thickness and a bending breaking resistance indicator of said bone from the mineral density and width of the bone;
    determining the wall/lumen ratio of the bone; and
    estimating the strength of said bone from the effective average cortical wall thickness, the wall/lumen ratio, and the bending breaking resistance indicator.

2. A method as defined in claim 1 wherein the mineral content of said bone is measured by photon absorptiometry.

3. A method as defined in claim 1 wherein the mineral content of said bone is measured by x-ray densitometry.

4. A method as defined in claim 1 wherein the mineral content of said bone is measured by determining the microdensity of a calibrated x-ray image of the bone.

5. A method as defined in claim 1 wherein:
    the effective average cortical wall thickness is determined from the formula CWT=Re—Ri where: Re is the effective outer radius of the bone, and Ri is the effective inner radius of the bone;
    the effective average outer radius of the bone is determined from the formula $$Re = \frac{D}{2} \times SF$$

where: D is the measured diameter of the bone and SF is the shape factor of the bone and the effective average outer radius of the bone is determined from the formula $$R_i = \sqrt{R_e^2 - \frac{BMC}{\pi \times SD \times L}}$$

where: BMC is the measured mineral content of the bone L is the length of a measured segment of the bone, and SD is a constant equaling the specific density of a particular long bone.

6. A method as defined in claim 5 wherein the bending breaking resistance indicator of the bone is calculated according to the formula $$BBRI = \frac{(Re^4 - R_i^4)}{Re}$$

where: BBRI is the bending breaking resistance indicator.

7. A method as defined in claim 1 wherein the wall/lumen ratio is determined according to the formula $$WLR = \frac{CWT}{R_i}$$

where: WLR is the wall/lumen ratio.

8. A method as defined in claim 1 wherein the bone mineral density, the wall/lumen ratio, the bending breaking resistance indicator, and the effective average cortical wall thickness of the bone are incorporated into a numerical presentation.

9. A method as defined in claim 8 wherein the bone mineral density, the wall/lumen ratio, the bending breaking resistance indicator, and the effective average cortical wall thickness of the bone are compared in the numerical presentation with values of those parameters for young normal bones and aged matched normal bones.

10. A method as defined in claim 8 wherein the change in bone mineral density between successive determinations of that parameter is incorporated in said presentation.

* * * * *